United States Patent [19]

Iwamoto et al.

[11] Patent Number: 4,782,100

[45] Date of Patent: Nov. 1, 1988

[54] PROSTHETIC COMPOSITION

[75] Inventors: Osamu Iwamoto, Yokohama; Toru Ono, Fujisawa; Koshi Kusumoto, Kamakura, all of Japan

[73] Assignee: Tokuyama Soda Kabushiki Kaisha, Yamaguchi, Japan

[21] Appl. No.: 7,611

[22] Filed: Jan. 28, 1987

[30] Foreign Application Priority Data

Jan. 31, 1986 [JP] Japan .................. 61-18043

[51] Int. Cl.⁴ .......................... C08F 265/06
[52] U.S. Cl. ...................... 522/120; 522/28; 525/305; 523/113; 523/116
[58] Field of Search .......... 522/120, 908, 14, 109; 525/305; 523/113, 116

[56] References Cited

U.S. PATENT DOCUMENTS

| 3,336,418 | 8/1967 | Dill | 525/305 |
| 4,134,809 | 1/1979 | Pacifici | 522/14 |
| 4,192,685 | 3/1980 | Horike | 430/283 |
| 4,311,624 | 1/1982 | Emmons | 428/463 |
| 4,485,161 | 11/1984 | Scozzafava | 522/14 |
| 4,525,258 | 6/1985 | Watanabe | 522/14 |
| 4,696,955 | 9/1987 | Kuhlman | 522/14 |

FOREIGN PATENT DOCUMENTS 1817716 12/1970 Fed. Rep. of Germany .

Primary Examiner—John C. Bleutge
Assistant Examiner—David Buttner
Attorney, Agent, or Firm—Sherman and Shalloway

[57] ABSTRACT

Disclosed is a prosthetic composition comprising (A) a diester monomer represented by the following formula:

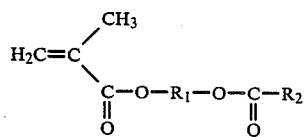

wherein
$R_1$ stands for an alkylene group having 2 to 6 carbon atoms and
$R_2$ stands for an alkyl group having 2 to 4 carbon atoms, or a mixture of said diester monomer and other monomer copolymerizable therewith, (B) an orgnic polymer soluble in the monomer (A) in an amount of 0.5 to 5 parts by weight per part by weight of said monomer (A) and (C) a radical polymerization initiator.

14 Claims, No Drawings

PROSTHETIC COMPOSITION

BACKGROUND OF THE INVENTION

The present invention relates to a novel prosthetic composition comprising a specific diester monomer.

A prosthetic agent is widely used in the dental field. For example, as the prosthetic agent for an artificial tooth or denture base, the relining material or the self-curing resin for repairing, there has been used a two-component type prosthetic agent comprising a polymer component such as polymethyl methacrylate (hereinafter referred to as "PMMA"), polyethyl methacrylate (hereinafter referred to as "PEMA") or a methyl methacrylate/ethyl methacrylate copolymer (hereinafter referred to as "PMMA-PEMA") and a monomer component such as methyl methacrylate (hereinafter referred to as "MMA") or ethylmethacrylate. In this two-component type prosthetic agent, two components are mixed and the mixture is cured by a radical initiator to form a dental prosthetic material. In the above-mentioned prosthetic composition, the monomer component can dissolve the polymer component in a short time. Accordingly, the monomer component and polymer component are homogeneously mixed and therefore, the mechanical properties of the obtained dental prosthetic material can be improved. Furthermore, if the viscosity of the mixture of the monomer component and polymer component is appropriately adjusted, the clinical or technical operation can be facilitated.

Methyl methacrylate as the main compound of the monomer component involves problems in that (1) it has a strong stimulant smell, (2) it gives a strong stimulus to the oral mucosa or the skin and (3) generation of heat at the polymerization is violent. As the prosthetic agent for solving these problems, there has been marketed a product comprising a monomer composed mainly of isobutyl methacrylate or butyl methacrylate. In this prosthetic agent, the problem of generation of heat is solved, but the problem of the stimulus is not sufficiently solved and a further improvement is desired.

West Germany Laid-Open Pat. No. 1,817,716 discloses 2-acetoxyethyl acrylate or 2-acetoxyethyl methacrylate, but it is merely taught that a gel formed by polymerizing this compound is used for the gel chromatography. When an experiment was carried out by using this acrylate compound as the monomer component of the prosthetic composition, it was found that the monomer has a stimulant smell and gives a stimulus to the tongue and the composition cannot be practically used.

SUMMARY OF THE INVENTION

It is therefore a primary object of the present invention to provide a monomer for the prosthetic agent, which is capable of dissolving a polymer in a short time and has no smell or a very weak smell.

Another object of the present invention is to provide a prosthetic composition which has a much reduced stimulus to the oral mucosa or the skin and has no substantial smell and in which generation of heat is controlled at the polymerization.

Still another object of the present invention is to provide a dental prosthetic composition, especially a dental prosthetic composition excellent as the relining material for denture base.

Other objects and embodiments of the present invention will become apparent from the following description.

In accordance with the present invention, the foregoing objects can be attained by a prosthetic composition comprising (A) a diester monomer represented by the following general formula:

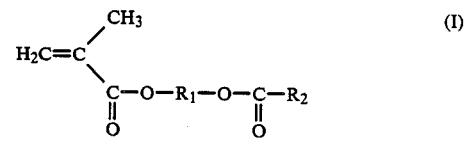

wherein
$R_1$ stands for an alkylene group having 2 to 6 carbon atoms and
$R_2$ stands for an alkyl group having 2 to 4 carbon atoms, or a mixture of said diester monomer and other monomer copolymerizable therewith, (B) an organic polymer soluble in the monomer (A) in an amount of 0.5 to 5 parts by weight per part by weight of said monomer (A) and (C) a radical polymerization initiator.

DETAILED DESCRIPTION OF THE PREFERRED EMBODIMENTS

The first component of the prosthetic composition of the present invention is a diester monomer represented by the following general formula (I):

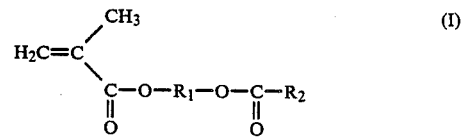

wherein
$R_1$ stands for an alkylene group $R_2$ having 2 to 6 carbon atoms and
$R_2$ stands for an alkyl group having 2 to 4 carbon atoms, or a mixture of said diester monomer and other monomer copolymerizable therewith.

In view of the properties necessary for the dental prosthetic agent, that is, the mechanical strength of the prosthetic material obtained by the polymerization, the lowly stimulating property to the skin or the oral mucosa and the polymer-dissolving property in the two-component type prosthetic agent and also in view of the industrial preparation, it is important that the monomer used in the present invention should be an acyloxyalkyl methacrylate represented by the above-mentioned general formula (I).

$R_1$ in the general formula (I) stands for an alkylene group having 2 to 6 carbon atoms, preferably 2 to 4 carbon atoms.

$R_2$ in the general formula (I) stands for an alkyl group having 2 to 4 carbon atoms. A compound in which $R_2$ is a methyl group is not preferred because the stimulus to the oral mucosa and the skin is strong and the compound has a smell. If the carbon number of $R_2$ is increased beyond the range specified in the present invention, the mechanical strength and the polymer-dissolving property are reduced and the industrial preparation of the ester becomes difficult.

Preferred examples of the alkylene group $R_1$ in the general formula (I) are

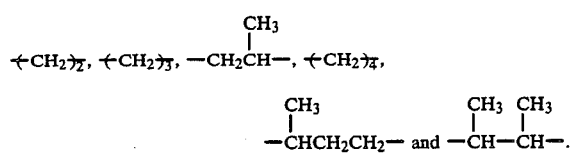

Preferred examples of the alkyl group in the general formula (I) are

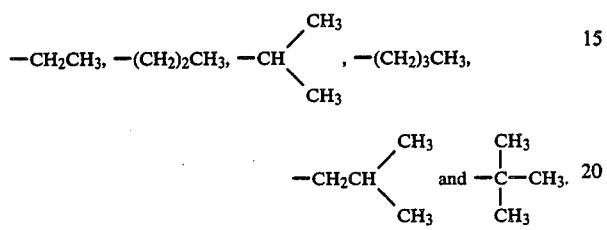

Preferred examples if the diester monomer of the general formula (I) used in the present invention are as follows:

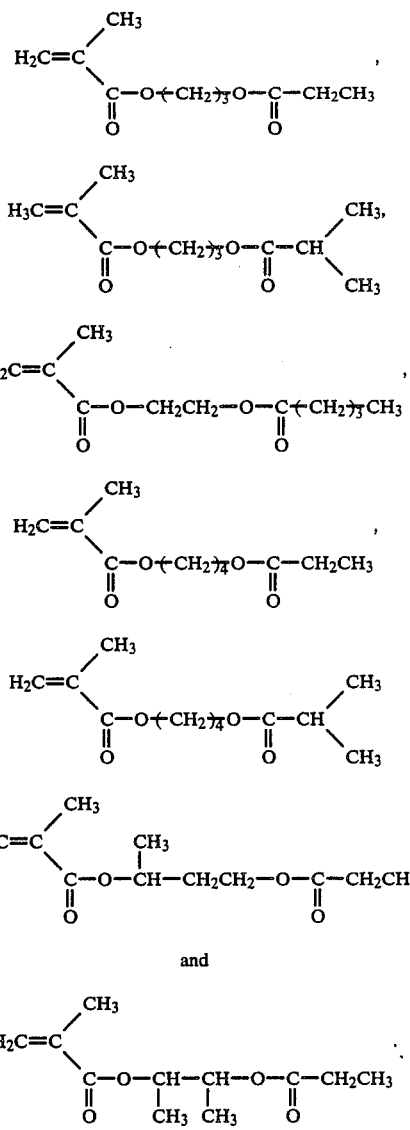

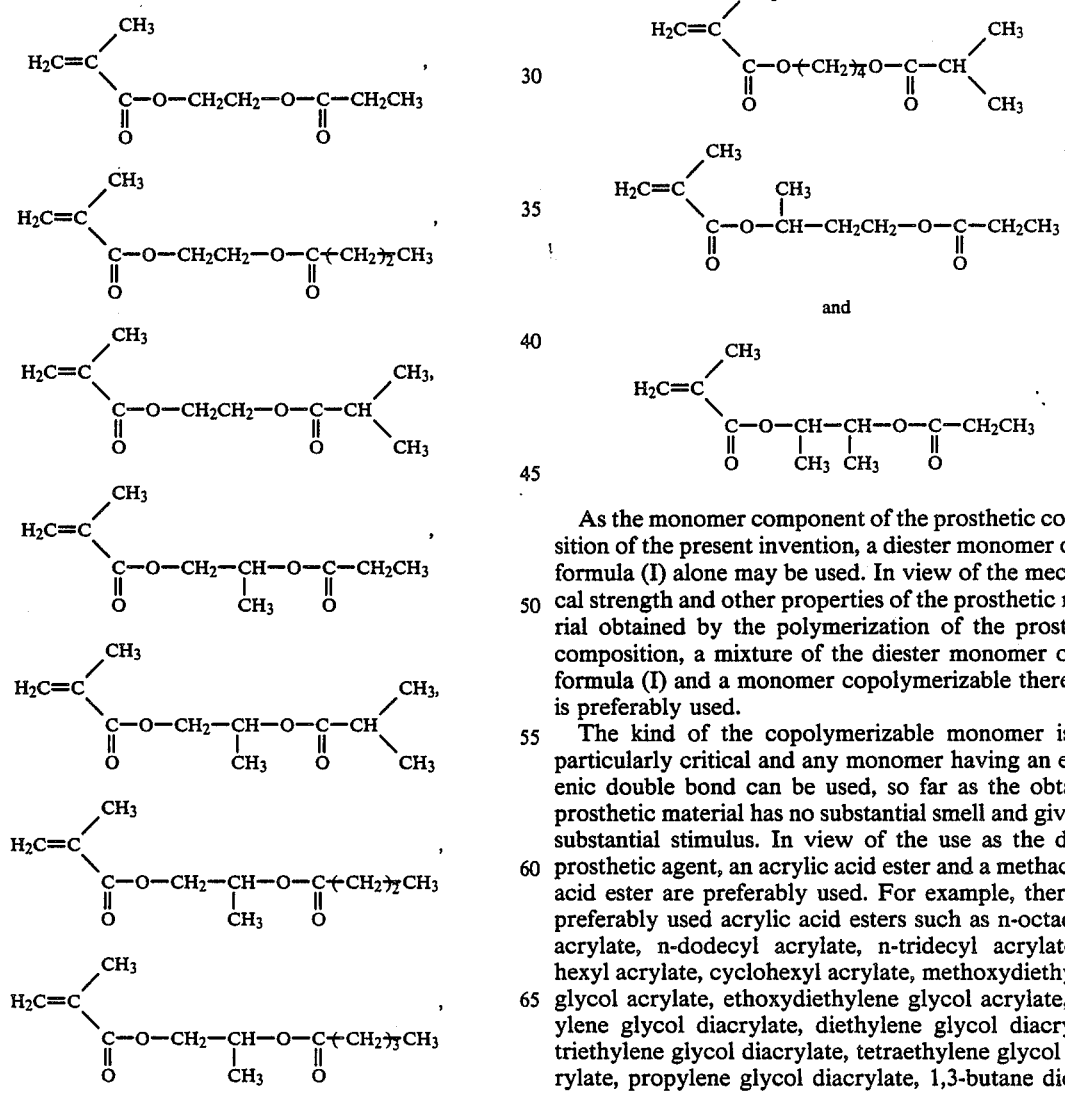

As the monomer component of the prosthetic composition of the present invention, a diester monomer of the formula (I) alone may be used. In view of the mechanical strength and other properties of the prosthetic material obtained by the polymerization of the prosthetic composition, a mixture of the diester monomer of the formula (I) and a monomer copolymerizable therewith is preferably used.

The kind of the copolymerizable monomer is not particularly critical and any monomer having an ethylenic double bond can be used, so far as the obtained prosthetic material has no substantial smell and gives no substantial stimulus. In view of the use as the dental prosthetic agent, an acrylic acid ester and a methacrylic acid ester are preferably used. For example, there are preferably used acrylic acid esters such as n-octadecyl acrylate, n-dodecyl acrylate, n-tridecyl acrylate, n-hexyl acrylate, cyclohexyl acrylate, methoxydiethylene glycol acrylate, ethoxydiethylene glycol acrylate, ethylene glycol diacrylate, diethylene glycol diacrylate, triethylene glycol diacrylate, tetraethylene glycol diacrylate, propylene glycol diacrylate, 1,3-butane diol diacrylate, 1,4-butane diol diacrylate, 1,6-hexane diol diacrylate, neopentyl glycol diacrylate, 1,10-decane diol acrylate, bisphenol-A diacrylate, 2,2'-bis(acryloyloxypolyethoxyphenyl)propane, 2,2'-bis(4-(3-acryloyloxy-2-hydroxypropoxy)phenyl)propane, trimethylol propane acrylate, trimethylol ethane triacrylate, tetra-methylol methane tetraacrylate and urethane diacrylate (reaction product of hydroxyethyl acrylate and 2,2,4-trimethylhexyl-1,6-diisocyanate), and methacrylic acid esters such as n-octadecyl methacrylate, n-dodecyl methacrylate, n-tridecyl methacrylate, n-hexyl methacrylate, cyclohexyl methacrylate, methoxydiethylene glycol methacrylate, ethoxydiethylene glycol methacrylate, ethylene glycol dimethacrylate, diethylene glycol dimethacrylate, triethylene glycol dimethacrylate, tetraethylene glycol dimethacrylate, propylene glycol dimethacrylate, 1,3-butane diol dimethacrylate, 1,4-butane diol dimethacrylate, 1,6-hexane diol dimethacrylate, neopentyl glycol dimethacrylate, 1,10-decane diol methacrylate, bisphenol-A dimethacrylate, 2,2'-bis(methacryloyloxypolyethoxyphenyl)propane, 2,2'-bis(4-(3-methacryloyloxy-2-hydroxypropoxy)phenyl)propane, trimethylol propane methacrylate, timethylol ethane trimethacrylate, tetramethylol methane tetramethacrylate and urethane dimethacrylate (reaction product of hydroxyethyl methacrylate and 2,2,4-trimethylhexyl-1,6-diisocyanate).

In the monomer component of the prosthetic composition of the present invention, the proportion of the diester monomer of the general formula (I) is appropriately selected. Generally, the proportion of the diester monomer of the formula (I) is 5 to 100% by weight based on the total monomer component, and it is preferred that the proportion of the diester monomer of the general formula (I) be 10 to 100% by weight, especially 20 to 100% by weight, based on the total monomer component.

The second component of the prosthetic composition of the present invention is an organic polymer component soluble in the above-mentioned monomer or monomer mixture. Any polymer soluble in the monomer or monomer mixture can be used without any limitation. In view of the chemical stability and transparency, PEMA, PMMA, PEMA-PEMM, polystyrene, polyesters and polymers of the above-mentioned acrylic acid esters or methacrylic acid esters are preferably used. PEMA has a high solubility and is preferably used. In the present invention, PEMA, PMMA-PEMA and polymer mixtures comprising such organic polymers as the main component are preferably used.

The molecular weight of the organic polymer is not particularly critical. However, in view of the mechanical strength of the formed dental prosthetic material and the solubility of the organic polymer, it is preferred that the molecular weight of the organic polymer be in the range of from 50,000 to 1,000,000. In order to improve the solubility of the polymer in the diester monomer, is is preferred that the particle size of the polymer be 10 to 100 μm.

The amount incorporated of the polymer may be selected within a broad range according to need. In order to improve the mechanical strength of the obtained prosthetic material, it is generally preferred that the amount of the polymer be 0.5 to 5 parts by weight, especially 1 to 2 parts by weight, per part by weight of the total monomer component.

The third component of the prosthetic composition of the present invention is a radical polymerization initiator. Various radical polymerization initiators can be used according to the curing method, and the kind and amount of the radical polymerization initiator cannot be simply specified. However, it is preferred that the radical polymerization initiator is used in an amount of 0.05 to 5% by weight, especially 0.1 to 2% by weight, based on the total monomer component.

Radical polymerization initiators preferably used in the present invention and preferred amounts thereof will now be described.

Radical polymerization initiators generating radicals at room temperature or under heating and radical polymerization initiators generating radicals under irradiation are preferably used in the present invention.

As the radical polymerization initiator generating radicals under heating, there are preferably used peroxides and azo compounds. Known peroxides can be used without any limitation. For example, there are preferably used dibenzoyl peroxide, 2,4-dichlorobenzoyl peroxide and dilauroyl peroxide. As the azo compound, there are preferably used 2,2'-azobisisobutyronitrile, 4,4'-azobis(4-cyanovaleric acid) and 2,2'-azobis(2,4-dimethylvaleronitrile). The curing temperature is changed according to the kind of the said catalyst, but it is preferred that the polymerization temperature be 40° to 150° C., especially 50° to 130° C.

A combination of a peroxide and a curing promoter represented by an amine or its salt can be used as the radical polymerization initiator generating radicals at room temperature. Known peroxides and known amines or its salts can be used without any limitation. As the peroxide, there may be used compounds as mentioned above. Secondary or tertiary amines having an amino group bonded to an aryl group are preferably used as the amine from the viewpoint of the curing velocity. For example, there are preferably used N,N'-dimethylaniline, N,N'-dimethyl-p-tolidine and N-methyl-N'-β-hydroxyethylaniline. These amines may be in the form of salts with hydrochloric acid, acetic acid, phosphoric acid or an organic acid.

In this radical polymerization initiator, it is preferred that the amount of each of the peroxide and the amine is 0.05 to 5% by weight, especially 0.1 to 2% by weight, based on the total monomer component.

Various radical polymerization initiators generating radicals under irradiation can be used. Any of known photosensitizers can be used. However, there are preferably used α-diketones such as diacetyl, acetylbenzoyl, benzoyl, benzyl, caamphorquinone, 9,10-phenanthroquinone and acenaphthenequinone, benzoin alkyl ethers such as benzoin methyl ether, benzoin ethyl ether and benzoin propyl ether, thioxanthone compounds such as 2,4-diethoxythioxanthone and methylthioxanthone, and benzophenone compounds such as benzophenone, p,p'-dimethylaminobenzophenone and p,p'-methoxybenzophenone.

In case of the photopolymerization, a curing promoter may be added together with the photosensitizer. As the curing promoter, there are preferably used amine compounds such as dimethyl-p-toluidine, N,N'-dimethylbenzylamine, N-methyldibutylamine and dimethylaminoethyl methacrylate, phosphite compounds such as dimethyl phosphite and dioctyl phosphite, cobalt compounds such as cobalt naphthenate, and barbituric acid. It is preferred that the amount of each of the photosensitizer and the curing promoter is 0.05 to 5% by weight, especially 0.1 to 1% by weight.

In case of the photopolymerization, curing is effected by ultraviolet rays of a high-pressure, medium-pressure or low-pressure mercury lamp or visible rays of a halogen lamp or xenone lamp.

In order to control the mechanical strength of the obtained prosthetic material, an inorganic filler, an alcohol such as ethanol and a plasticizer such as dibutyl phthalate, dioctyl phthalate, butylbenzyl phthalate, dibutyl sebacate, glycerol triacetate, dibutyl maleate or dioctyl maleate may be added to the prosthetic composition comprising the above-mentioned indispensable components.

It is preferred that a small amount of a polymerization inhibitor such as hydroquinone, hydroquinone monomethyl ether r butylhydroxytoluene be added to the prosthetic composition of the present invention.

The mode of use of the prosthetic composition of the present invention is not particularly critical. In general, the prosthetic composition is used in the form of a separated package in which the polymer component and the monomer component are separately packaged and small amounts of both the components are taken out from packages at the time of application and they are mixed and kneaded to effect curing, or a single package in which all the components are packaged in one pack. The separated package and the single package are appropriately selected according to need. In general, in the case where a radical initiator of the room temperature polymerization type is used as the catalyst, the separated package is adopted and the peroxide as the catalyst and the amine or its salt are packaged in different packs. In the case where other catalyst, for example, a catalyst causing curing under irradiation with light or by heating, is used, either the separated package or the single package can be adopted. Ordinarily, in case of the separated package, initial viscosity on mixing of both the components is low, and therefore, the separated package is used for the prosthesis where a flowability is necessary. On the other hand, the single package is preferably used for the prosthesis where a flowability is not particularly necessary. The prosthetic composition of the present invention can be used as a resin for a denture base, a selfcuring resin for a relining or a rebase, a selfcuring resin for repairing an artificial tooth, a selfcuring resin for a tooth crown, a selfcuring resin for a tray, a rapid selfcuring resin, a hard crown and bridge resin, a soft resin for a denture base and a orthodontic resin.

Since the diester monomer represented by the general formula (I) has a high polymer-dissolving ability, the powder component is smoothly dissolved in a good condition and a prosthetic material excellent in the mechanical strength can be obtained by the polymerization. Furthermore, since the diester monomer has substantially no smell or a very weak stimulant smell and the stimulus to the oral mucosa and the skin is very weak, even if this diester monomer is used, an unpleasant feeling owing to a smell or stimulus to the mucosa is not given to a patient.

Accordingly, the monomer component of the prosthetic composition of the present invention is very excellent in the dental field and the practical value of the prosthetic composition of the present invention is very high.

The present invention will now be described in detail with reference to the following examples that by no means limit the scope of the invention.

The following abbreviations are used to indicate diester monomers used in the examples and comparative examples.

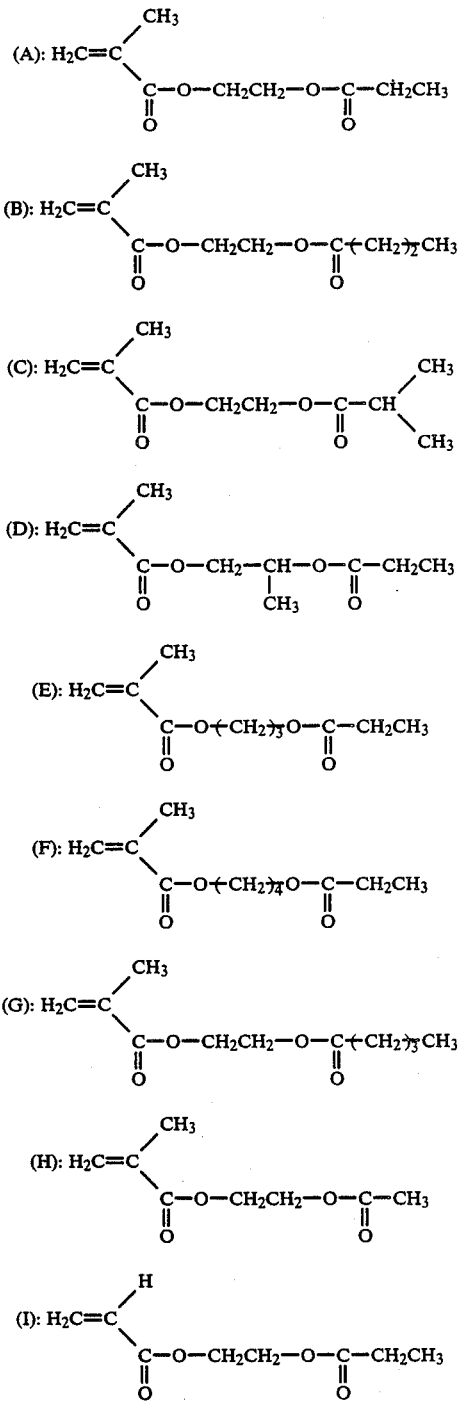

Example 1

The stimulus to the skin, the smell and the polymer-dissolving ability were tested with respect to diester monomers shown in Table 2.

The stimulating property was tested according to two methods. One method is a so-called Draize method and the other method is a method for measuring a sense of pain on the tongue.

The Draize method was carried out in the following manner.

An Angora rabbit was shorn on the back by hair clippers, and 0.05 ml of a sample was coated on the left side of the shorn skin surface and 0.05 ml of a reference sample was coated on the right side of the shorn skin surface, and after 24 hours, the inflammation state was evaluated according to the standard shown in Table 1.

to 1.6, and the viscosity increase was determined with respect to various esters.

In the case where MMA was used as the monomer, the speed of increase of the viscosity was too high. Accordingly, in this case, PMMA (having an average molecular weight of 250,000 and an average particle size of 30 μm) was used as the polymer.

The measurement results are shown in Table 2.

TABLE 2

| Run No. | Monomer | Smell | Stimulus Draize method | Stimulus to tongue | Solubility Viscosity (poise) after 4 minutes | Viscosity (poise) after 6 minutes |
|---|---|---|---|---|---|---|
| 1 | diester monomer (A)' | slight smell | 3.0 | very slight pain | 8500 | 12000 |
| 2 | diester monomer (B) | slight smell | 2.7 | very slight pain | 900 | 5000 |
| 3 | diester monomer (C) | slight smell | 2.7 | very slight pain | 800 | 4500 |
| 4 | diester monomer (D) | slight smell | 2.5 | very slight pain | 1200 | 6700 |
| 5 | diester monomer (E) | slight smell | 2.5 | very slight pain | 1400 | 7200 |
| 6 | diester monomer (F) | slight smell | 2.2 | very slight pain | 700 | 3700 |
| 7 | diester monomer (G) | slight smell | 2.1 | very slight pain | 500 | 2100 |
| 8 | deister monomer (I) | slight smell | 5.6 | strong pain | 9500 | 14000 |
| 9 | MMA | strong stimulus smell | 3.7 | very strong pain | 4000 | 9000 |
| 10 | isobutyl methacrylate | strong stimulus smell | 4.0 | strong pain | 2500 | 12000 |
| 11 | decane diol dimethacrylate | slight smell | 1.8 | very weak pain | ≈0 | ≈0 |

Note
Runs Nos. 8 through 11 are comparative runs.

The test was conducted on at least 6 rabbits, and an average point was calculated. The smaller is the average point, the smaller is the stimulus to the skin.

TABLE 1

| Evaluation of Draize Skin Reaction | |
|---|---|
| Skin Reaction | Evaluation Point |
| (1) Formation of Rash and Crust | |
| no rash | 0 |
| very slight rash | 1 |
| definite rash | 2 |
| medium-to-strong rash | 3 |
| strong rash with crust | 4 |
| (2) Formation of Edema | |
| no edema | 0 |
| very slight edema | 1 |
| slight edema (definite protuberance) | 2 |
| medium edema (about 1 mm protuberance) | 3 |
| strong edema (protuberance larger than 1 mm) | 4 |
| Skin-Stimulating Property | sum of points (1) and (2) |

The test of the sense of pain was carried out in the following manner. Namely, one drop of the diester monomer was dropped on the tip of the tongue, and after 1 minute, the sense of pain was evaluated.

The polymer-dissolving velocity of the monomer was measured in the following manner. Namely, in view of the operation adaptability in the practical application, the increase of the viscosity (at 23° C.) after mixing of the polymer and monomer was measured by a cone plate type viscometer (High-Shear Rheometer Model IGK-1 supplied by Ishida Giken), and the change of the viscosity with the lapse of time was recorded by an X-Y plotter.

PEMA (having an average molecular weight of 250,000 and a spherical shape having an average particle size of 30 μm) was used as the polymer. The weight ratio of the polymer and the diester monomer was fixed Example 2

A polymer component having a composition (1) shown below was mixed with a monomer component having a composition (2) shown below at a weight ratio of 1.6, and after 1 minute had passed from the time of mixing, the skin-stimulating property and smell were tested in the same manner as described in Example 1. The obtained results are shown in Table 3.

| (1) Polymer Component | |
|---|---|
| PEMA (having average molecular weight of 500,000 and average particle size of 30 μm) | 80 parts by weight |
| PMMA (having average molecular weight of 500,000 and average particle size of 30 μm) | 20 parts by weight |
| Camphorquinone | 0.5 part by weight |
| (2) Monomer Component | |
| Diester monomer | 40 parts by weight |
| Hexanediol dimethacrylate | 60 parts by weight |
| Hydroquinone monomethyl ether | 0.05 part by weight |
| N,N'—Dimethyl-p-toluidine | 0.5 part by weight |

TABLE 3

| Run No. | Monomer | Smell | Stimulus Draize Method | Stimulus to Tongue |
|---|---|---|---|---|
| 1 | diester (A) | slight smell | 1.0 | no pain |
| 2 | diester (B) | slight smell | 0.8 | no pain |
| 3 | diester (C) | slight smell | 0.8 | no pain |
| 4 | diester (D) | slight smell | 0.7 | no pain |
| 5 | diester (E) | slight smell | 0.7 | no pain |
| 6 | diester (F) | slight smell | 0.7 | no pain |
| 7 | diester (G) | slight smell | 0.7 | no pain |
| 8 | MMA | strong stimulant smell | 2.5 | very strong pain |
| 9 | isobutyl methacrylate | strong stimulant smell | 2.7 | strong pain |

TABLE 3-continued

| Run No. | Monomer | Smell | Draize Method | Stimulus to Tongue |
|---------|---------|-------|---------------|--------------------|
| 10 | diester (H) | stimulant smell | 1.8 | weak pain |

Note
Runs Nos. 8 through 10 are comparative runs.

Example 3

The dental prosthetic agent of the present invention was polymerized by a radical polymerization initiator shown in Table 4, and the bending strength of the obtained polymer was measured. A mixture comprising a polymer component having a composition (3) shown below and a monomer component having a composition (4) shown below at a weight ratio of 1.6 was used as the prosthetic composition. After mixing, the mixture was cast in a mold having a length of 80 mm, a width of 50 mm and a thickness of 4 mm and polymerized under a nitrogen atmosphere at room temperature or under heating. The formed plate was cooled and a sample having a length of 70 mm, a width of 10 mm and a thickness of 2.5 mm was cut out and polished to obtain a measurement sample. The measurement sample was allowed to stand still at 23° C. for 24 hours. The bending test was carried out by a tensile tester while adjusting the distance between fulcrums to 50 mm. The cross head speed was 0.5 mm/min.

The obtained results are shown in Table 4.

| (3) Polymer Component | |
|---|---|
| PEMA (having average molecular weight of 500,000 and average particle size of 30 μm) | 40 parts by weight |
| PMMA (having average molecular weight of 500,000 and average particle size of 30 μm) | 60 parts by weight |
| Radical polymerization initiator | 1.0 part by weight |
| Pigment | 0.05 part by weight |
| (4) Monomer Component | |
| Diester Monomer | 40 parts by weight |
| Hexane diol dimethacrylate | 60 parts by weight |
| Hydroquinone monomethyl ether | 0.05 part by weight |
| Curing promoter | 1.0 part by weight |

TABLE 4

| Run No. | Diester Monomer | Radial Polymerization Initiator | Curing Promoter | Bending Strength (kg/cm²) | Remarks |
|---------|-----------------|--------------------------------|------------------|---------------------------|---------|
| 1 | A | 2,2'-azobisisobutyronitrile | — | 790 | heated at 85° C. |
| 2 | A | 4-cyanovaleric acid | — | 770 | heated at 85° C. |
| 3 | A | azobisdimethylvaleronitrile | — | 770 | heated at 85° C. |
| 4 | B | decanoyl peroxide | — | 760 | heated at 100° C. |
| 5 | C | lauroyl peroxide | — | 790 | heated at 100° C. |
| 6 | A | benzoyl peroxide | N,N'—di(β-hydroxyethyl)-p-toluidine | 650 | polymerized at room temperature |
| 7 | B | benzoyl peroxide | N,N'—di(β-hydroxyethyl)-p-toluidine | 660 | polymerized at room temperature |
| 8 | C | benzoyl peroxide | N,N'—dimethyl-p-toluidine | 640 | polymerized at room temperature |
| 9 | D | benzoyl peroxide | N,N'—dimethyl-p-toluidine | 620 | polymerized at room temperature |
| 10 | E | dilauroyl peroxide | N,N'—di(β-hydroxyethyl)-p-toluidine | 590 | polymerized at room temperature |
| 11 | F | dilauroyl peroxide | N,N'—di(β-hydroxyethyl)-p-toluidine | 570 | polymerized at room temperature |
| 12 | G | di-p-chlorobenzoyl peroxide | N,N'—di(β-hydroxyethyl)-p-toluidine | 590 | polymerized at room temperature |

When denture base and relining materials were prepared from compositions of Runs Nos. 1 through 12 shown in Table 4 by polymerization under heating or room temperature polymerization, denture base and relining material having a sufficient strength were obtained. When the compositions of Runs Nos. 6, 7 and 8 were used as the selfcuring resin for a tray and the rapid-selfcuring resin, tray and temporary teeth having sufficient properties could be obtained.

Example 4

A mixture of a polymer having a composition (5) shown below and a monomer component having a composition (6) shown below was cast in a mold in the same manner as described in Example 3 and the mixture was cured by irradiating for 20 minutes with rays of a commercially available visible ray irradiator (Triad Cure Unit supplied by Dentsply Co.). The bending test was carried out in the same manner as described in Example 3.

The obtained results are shown in Table 5.

| (5) Polymer Component | |
|---|---|
| PEMA (having average molecular weight of 500,000 and average particle size of 30 μm) | 80 parts by weight |
| PMMA (having average molecular weight of 500,000 and average particle size of 30 μm) | 20 parts by weight |
| Radical polymerization initiator | 0.5 part by weight |
| (6) Monomer Component | |
| Diester monomer | 50 parts by weight |
| Urethane dimethacrylate (reaction product of hydroxyethyl methacrylate and 2,2,4-trimethylhexyl-1,6-diisocyanate) | 50 parts by weight |
| Curing promoter | 0.5 part by weight |
| Malic acid | 0.1 part by weight |
| Butylhydroxytoluene | 0.05 part by weight |

TABLE 5

| Run No. | Diester Monomer | Radical Polymerization Initiator (parts by weight) | Curing Promoter (parts by weight) | Bending Strength (kg/cm$^2$) |
|---|---|---|---|---|
| 1 | A | camphorquinone (0.5) | N,N'—dimethyl-benzylamine (0.5) | 630 |
| 2 | B | benzyl (1.0) | N,N'—dimethyl-p-toluidine (0.5) | 640 |
| 3 | C | 2,4-diethoxythioxanthone (0.8) | N,N'—dimethyl-p-toluidine (0.4) | 600 |
| 4 | D | α-naphthyl (1.0) | dimethylaminoethyl methacrylate (1.0) | 620 |

When the compositions of Runs Nos. 1 through 4 were used as a relining of a denture base, a relining nent was changed to a monomer shown in Table 6. The obtained results are shown in Table 6.

TABLE 6

| Run No. | Diester Monomer | Polymer (parts by weight) | | Monomer (parts by weight) | | Polymer Component/ Monomer Component Weight Ratio | Bending Strength (kg/cm$^2$) |
|---|---|---|---|---|---|---|---|
| 1 | A | PEMA (average molecular weight = 250,000, average particle size = 30 μm) | (40) | 1,6-hexane diol dimethacrylate | (30) | 1.6 | 640 |
| | | PMMA (average molecular weight = 250,000, average particle size = 30 μm) | (60) | 1,10-decane diol dimethacrylate | (70) | | |
| 2 | B | PEMA (same as above) | (50) | neopentyl glycol dimethacrylate | (100) | 1.6 | 600 |
| | | polystyrene (average molecular weight = 1,000,000, average particle size = 10 μm) | (50) | | | | |
| 3 | C | PEMA (same as above) | (30) | neopentyl glycol dimethacrylate | (50) | 1.6 | 650 |
| | | PMMA-PEMA (average molecular weight = 500,000, average particle size = 50 μm) | (70) | bisphenol-A dimethacrylate | (50) | | |
| 4 | D | PEMA (same as above) | (50) | trimethylol propane methacrylate | (20) | 1.6 | 630 |
| | | poly-n-hexyl methacrylate (average molecular weight 200,000, average particle size = 10 μm) | (50) | urethane dimethacrylate | (80) | | |
| 5 | E | PEMA (same as above) | (60) | trimethylol propane methacrylate | (20) | 1.2 | 600 |
| | | poly-n-octadecyl methacrylate (average molecular weight = 100,000, average particle size = 10 μm) | (40) | urethane dimethacrylate | (80) | | |
| 6 | F | PEMA (same as above) | (20) | trimethylol propane methacrylate | (20) | 2.0 | 680 |
| | | polycyclohexyl methacrylate (average molecular weight = 80,000, average particle size = 30 μm) | (80) | urethane dimethacrylate | (80) | | |
| 7 | G | PEMA (same as above) | (70) | bisphenol A dimethacrylate | (100) | 1.8 | 660 |
| | | ethylene glycol dimethylacrylate polymer (average particle size = 50 μm) | (30) | | | | | having a good compatibility was obtained in each case.

Example 5

Polymerization was carried out in the same manner as in Run No. 6 of Example 3 except that PEMA and PMMA in the polymer component of Run No. 6 of Example 3 were changed to polymers shown in Table 6 and hexane diol dimethacrylate of the monomer compo-

Example 6

A dental prosthetic agent of the room temperature polymerization type was polymerized to form a prosthetic material having a rubbery elasticity, and the hardness was measured by the spring hardness test method (type A) according to JIS 6301 (physical test method for vulcanized rubber). A rectangular parallelepiped sample having a length of 20 mm, a width of 20 mm and a thickness of 15 mm was used for the measurement. The weight ratio of a polymer component having a composition (7) shown below and a monomer component having a composition (8) shown below was adjusted to 1. The composition of the dental prosthetic agent was as shown below.

| (7) Polymer Component | |
|---|---|
| PEMA (having average molecular weight of 250,000 and average particle size of 30 μm) | 100 parts by weight |
| Benzoyl peroxide | 1.0 part by weight |
| Pigment | 0.05 part by weight |
| (8) Monomer Component | |
| Diester monomer | 60 parts by weight |
| Tridecyl methacrylate | 40 parts by weight |
| Di-n-butyl phthalate | 20 parts by weight |
| N,N'—di(p-hydroxyethyl)-p-toluidine | 1 part by weight |
| Butylhydroxytoluene | 0.05 part by weight |

The obtained results are shown in Table 7.

TABLE 7

| Run No. | Diester monomer | Hardness |
|---|---|---|
| 1 | A | 80 |
| 2 | B | 72 |
| 3 | C | 75 |
| 4 | D | 73 |
| 5 | E | 70 |
| 6 | F | 65 |
| 7 | G | 71 |

When the prosthetic agents of Runs Nos. 1 through 7 were used as a soft resin for the relining of a denture base, a denture base having a good plasticity was obtained in each case.

We claim:

1. A prosthetic composition comprising (A) a diester monomer represented by the following general formula:

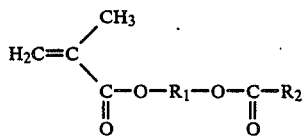

wherein
R$_1$ stands for an alkylene group having 2 to 6 carbon atoms and
R$_2$ stands for an alkyl group having 2 to 4 carbon atoms, or a mixture of said diester monomer and other monomer copolymerizable therewith, (B) an organic polymer soluble in the monomer (A) in an amount of 0.5 to 5 parts by weight per part by weight of said monomer (A), said organic polymer (B) comprising poly(methyl methacrylate), poly(ethyl methacrylate), poly(methyl methacrylate/ethyl methacrylate), mixtures of any of the foregoing with each other, or mixtures of any of the foregoing with other polymer soluble in said monomer (A), and (C) a radical polymerization initiator.

2. A prosthetic composition as set forth in claim 1, which is a mixture of the diester monomer and a copolymerizable methacrylic acid ester or an acrylic acid ester.

3. A prosthetic composition as set forth in claim 1, wherein the radical polymerization initiator is a combination of a peroxide and an amine compound.

4. A prosthetic composition as set forth in claim 1, wherein the radical polymerization initiator is a photosensitizer.

5. A prosthetic composition as set forth in claim 1, which is in the form of a separated package comprising a package of the polymer component and a package of the monomer component.

6. A prosthetic composition as set forth in claim 5, wherein a peroxide catalyst is contained in the package of the polymer component and an amine or its salt as a curing promoter is contained in the package of the monomer component.

7. A prosthetic composition as set forth in claim 1, which is in the form of a single package.

8. A prosthetic composition as set forth in claim 1, which is a relining material for a denture base.

9. A prosthetic composition as set forth in claim 1, wherein
R$_1$ stands for an akylene group having 2 to 4 carbon atoms selected from the group consisting of

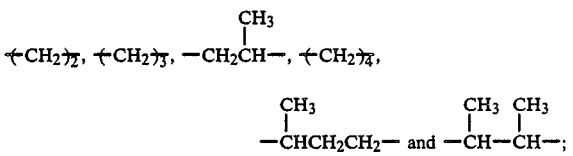

and
R$_2$ stands for an alkylene group selected from the group consisting of

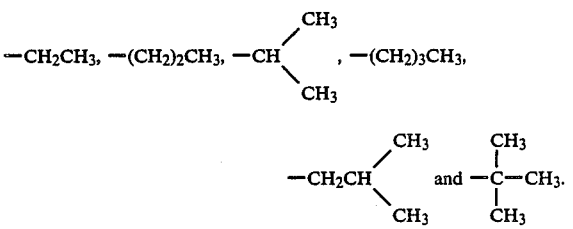

10. A prosthetic composition as set forth in claim 1 wherein the diester monomer is selected from the group consisting of

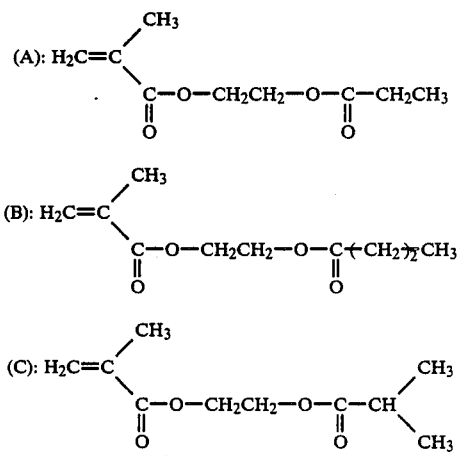

-continued

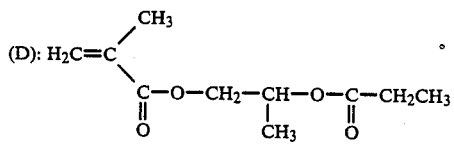

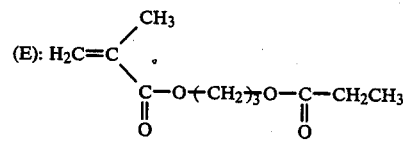

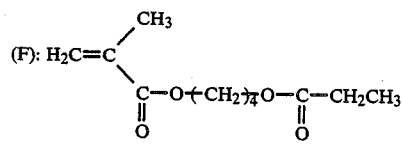

and

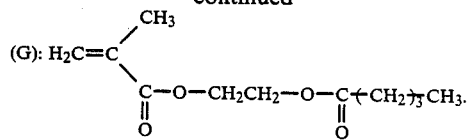

11. A prosthetic composition as set forth in claim 1, wherein the organic polymer (B) comprises a mixture of at least two of poly(methyl methacrylate), poly(ethyl methacrylate) and poly(methyl methacrylate/ethyl methacrylate).

12. A prosthetic composition as set forth in claim 1, wherein the organic polymer soluble in the monomer (A) has a molecular weight in the range of from 50,000 to 1,000,000.

13. A prosthetic composition as set forth in claim 1, wherein the organic polymer soluble in the monomer (A) has a particle size in the range of from 10 to 100 microns.

14. A prosthetic composition as set forth in claim 1, wherein the amount of the organic polymer (B) is from one to two parts by weight, per part by weight of the monomer component (A).

* * * * *